(12) United States Patent
Wu et al.

(10) Patent No.: US 7,576,860 B2
(45) Date of Patent: Aug. 18, 2009

(54) LIGHT FILTER HAVING A WEDGE-SHAPED PROFILE

(75) Inventors: Kuohua (Angus) Wu, Tucson, AZ (US); David L Erickson, Philomath, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 311 days.

(21) Appl. No.: 11/801,830

(22) Filed: May 11, 2007

(65) Prior Publication Data
US 2008/0278724 A1 Nov. 13, 2008

(51) Int. Cl.
*G01J 3/51* (2006.01)
(52) U.S. Cl. .......................... 356/419; 359/580; 359/589
(58) Field of Classification Search ................. 356/419; 359/589
See application file for complete search history.

(56) References Cited

U.S. PATENT DOCUMENTS

| | | | |
|---|---|---|---|
| 3,447,873 A | 6/1969 | Ashley et al. | |
| 3,498,693 A | 3/1970 | Felin et al. | |
| 3,552,826 A | 1/1971 | Hanes et al. | |
| 5,144,498 A | 9/1992 | Vincent | |
| 5,166,755 A | 11/1992 | Gat | |
| 5,227,648 A | 7/1993 | Woo | |
| 5,872,655 A | 2/1999 | Seddon et al. | |
| 5,940,182 A | 8/1999 | Lepper, Jr. et al. | |
| 6,057,925 A | 5/2000 | Anthon | |
| 6,278,522 B1 | 8/2001 | Lepper, Jr. et al. | |
| 6,292,299 B1 | 9/2001 | Liou | |
| 6,785,002 B2 | 9/2002 | Zarrabian et al. | |
| 6,940,593 B2 | 8/2003 | Farr | |
| 6,630,999 B2 | 11/2003 | Shroder | |
| 6,678,093 B1 | 1/2004 | Scobey et al. | |
| 6,700,690 B1 | 3/2004 | Buchsbaum et al. | |
| 6,947,218 B2 | 3/2004 | Turner, III | |
| 6,791,758 B1 | 9/2004 | Scobey | |
| 7,071,457 B2 | 1/2005 | Farr | |
| 7,064,828 B1 | 6/2006 | Rovira et al. | |
| 2007/0148760 A1* | 6/2007 | Klesel et al. | ............ 435/287.2 |

FOREIGN PATENT DOCUMENTS

JP 2006-301487 A 11/2006

* cited by examiner

*Primary Examiner*—F. L Evans

(57) ABSTRACT

A light filter includes exactly one partially reflective layer having a top and a bottom and a wedge-shaped profile defining a wedge direction. First and second transparent layers are disposed on the top and bottom, respectively, of the partially reflective layer, each transparent layer including at least two dielectric layers of two different materials, each dielectric layer having a wedge-shaped profile oriented in the wedge direction. A photospectrometer including a light filter with the wedge-shaped profile is also disclosed.

20 Claims, 3 Drawing Sheets

LIGHT FILTER HAVING A WEDGE-SHAPED PROFILE

BACKGROUND

A photospectrometer is an instrument used for measuring wavelengths of light digitally, so that shades of color can be accurately detected. One type of filter that can be used with a solid state photospectrometer is a Fabry-Perot filter. Using current fabrication methods it can be relatively complicated and costly to fabricate a photospectrometer having an array of Fabry-Perot filters of unique thicknesses affixed atop addressable photodiodes due to multiple etching and deposition steps used to obtain an array of transparent layers with different thicknesses.

BRIEF DESCRIPTION OF THE DRAWINGS

Various features and advantages of the present disclosure will be apparent from the detailed description which follows, taken in conjunction with the accompanying drawings, which together illustrate, by way of example, features of the present disclosure, and wherein.

DETAILED DESCRIPTION

Figure 1:
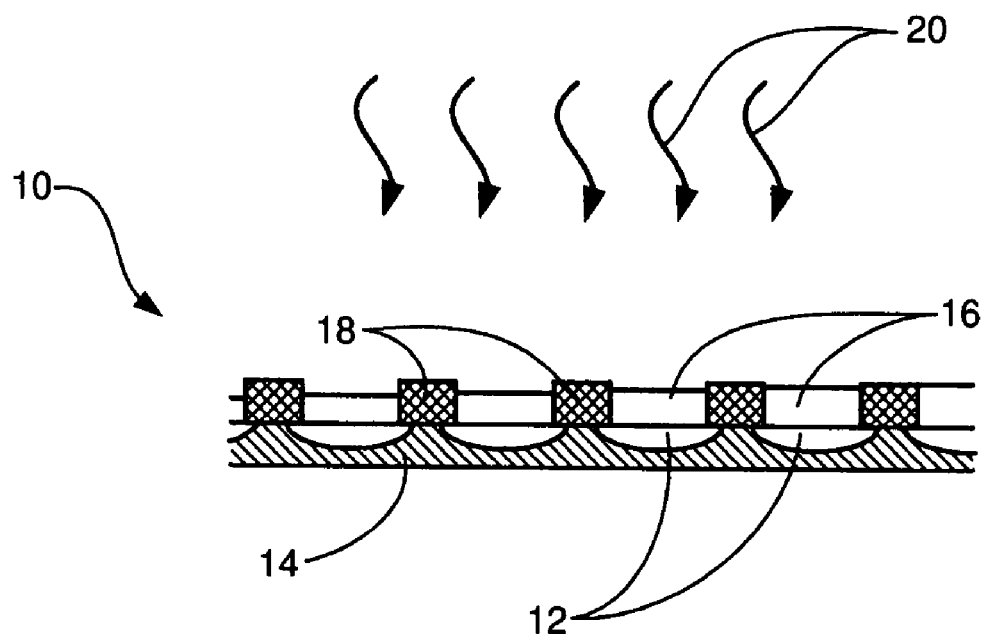
FIG. 1 is a partial cross-sectional view of a solid state photospectrometer comprising an array of photodiodes, with each photodiode having a unique light filter.

Reference will now be made to exemplary embodiments illustrated in the drawings, and specific language will be used herein to describe the same. It will nevertheless be understood that no limitation of the scope of the present disclosure is thereby intended. Alterations and further modifications of the features illustrated herein, and additional applications of the principles illustrated herein, which would occur to one skilled in the relevant art and having possession of this disclosure, are to be considered within the scope of this disclosure.

The present disclosure relates to solid-state light filters, such as are frequently used with photospectrometers. As noted above, photospectrometers are frequently used in the printing arts to calibrate digital color printing systems and to help measure the color match quality of printed output. For accurate color detection and calculation, it is desirable that the photospectrometer detect numerous narrow light transmission bands.

One common approach for creating a photospectrometer that detects a series of high and narrow transmission bands is to use an array of filters positioned over photodiodes. In such a photospectrometer the filters are integrated with the photodiode array. Shown in FIG. 1 is one embodiment of a photospectrometer 10 having a plurality of photodiodes 12 mounted on a substrate 14. Each photodiode is provided with a discrete filter 16 that allows only a certain wavelength band of the incident light 20 to be passed to that photodiode, so that light intensity across a spectrum is detected. In other words, each photodiode can detect the intensity of light of a given wavelength depending upon the characteristics of its particular filter. Adjacent filters are separated by spacer material 18 that prevents light leakage between adjacent photodiodes.

Figure 2:
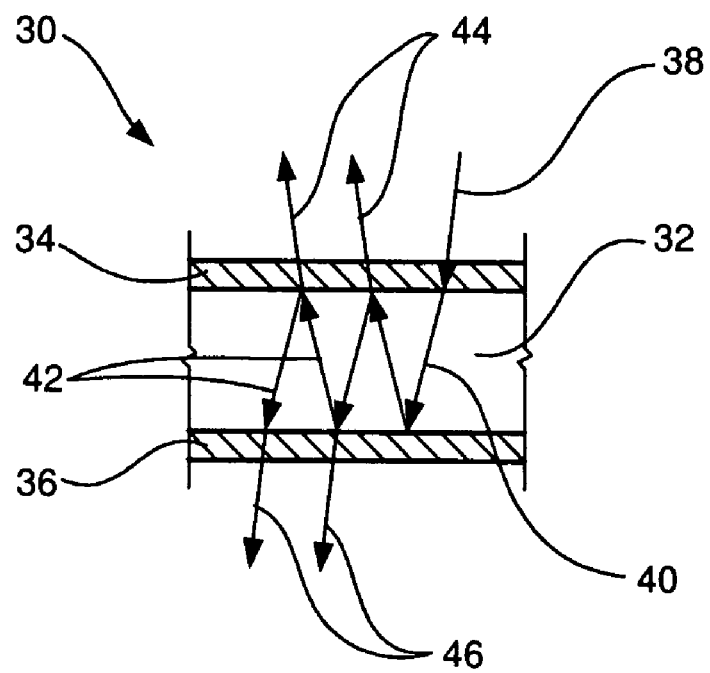
FIG. 2 is a partial cross-sectional view of a typical Fabry-Perot filter.

One type of filter that can be used with this type of device is a Fabry-Perot filter. Fabry-Perot filters are widely used in telecommunications, lasers and spectroscopy for controlling and measuring the wavelength of light. One embodiment of a Fabry-Perot filter 30 is shown in FIG. 2. This filter includes a transparent layer 32 that is sandwiched between two parallel, partially reflective layers 34 and 36. The transparent layer 32 that separates the partially reflective layers 34, 36 is frequently a dielectric material, such as silicon dioxide, aluminum oxide, titanium dioxide, zinc oxide, tellurium oxide, etc. A variety of materials can be used for the partially reflective layers, including metals such as aluminum, copper, silver, gold, etc. Metals are generally good reflectors, though they differ in absorption characteristics at different wavelengths. Silver is frequently used for the metal layers in a Fabry-Perot filter because silver has relatively high reflectivity and exhibits less absorption than some other metals in the visible spectrum. The thickness and nature of the top partially reflective metal layer (i.e. what kind of metal) will initially determine what wavelengths of light will enter the transparent (e.g. dielectric) layer, and the transmission efficiency of the filter. The transparent material that separates the reflective surfaces is often chosen to maintain stable mirror-to-mirror distances, and to keep stable frequencies even when the temperature varies.

Incoming light 38 that passes through the top partially reflective layer is initially refracted, as indicated at 40, and then reflects internally between the two partially reflective layers, as indicated at 42. Through interference between the internally reflecting light, certain wavelengths will be absorbed or reflected out of the filter, as indicated at 44, while light of other wavelength(s) will be passed through the bottom partially reflective layer, as indicated at 46. The varying transmission function of a Fabry-Perot filter is caused by interference between the multiple reflections of light between the two reflecting surfaces. Constructive interference occurs if the transmitted beams are in phase, and this corresponds to a high-transmission peak of the filter. If the transmitted beams are out-of-phase, destructive interference occurs, and this corresponds to a transmission minimum. Whether the multiply-reflected beams are in-phase or not depends on the wavelength of the light, the angle the light travels through the filter, the thickness of the dielectric layer, and the refractive index of the dielectric layer. Ultimately, only a certain wavelength band of light will pass through the bottom metal layer.

The transmission spectrum of a Fabry-Perot filter as a function of wavelength exhibits peaks of large transmission corresponding to resonances of the filter. The shape of the wavelength peak that is passed by a given Fabry-Perot filter is quanitfied by a characteristic called finesse. Fabry-Perot filters with high finesse show sharper transmission peaks with lower minimum transmission coefficients. However, it can be difficult to obtain high finesse (high transmission and narrow bandwidth) in a standard Fabry-Perot filter. If a given filter has low transmission and wide bandwidth, there will be a smaller transmission band in the visible spectrum. In order to achieve high finesse, it is desirable that the partial reflective layers should also have high reflectivity. Thicker metallic layers will provide better internal reflectivity, but thicker metallic layers will also absorb light. Thinner metallic layers allow more light transmission, but thin metallic layers provide less internal reflectivity, which increases the need for high finesse. Consequently, high finesse in a Fabry-Perot filter is difficult to obtain because thicker metal layers will provide a narrower bandwidth but will reduce transmission, while thinner metal layers increase transmission of light, but provide a wider bandwidth due to lower internal reflectivity. It is thus difficult to obtain both high transmission and a narrow bandwidth with a Fabry-Perot filter using metals as the partially reflective layers.

Additionally, using an array of fixed Fabry-Perot filters over photodiodes presents some other undesirable aspects. As is apparent from FIG. 1, a discrete filter of a particular thickness is used for each desired wavelength. Consequently, this approach requires multiple etching and deposition steps to obtain an array of transparent spacer layers with different thicknesses. Where the total number of desired transmission bands is $2^n$, the number of etching and deposition process cycles will be n+1. Thus, for example, if detection of 16 discrete wavelength bands is desired, the value of n will be 4 (because $2^4$=16), and the total number of deposition/etch fabrication cycles for the Fabry-Perot filter layers will thus be 5, with each cycle involving multiple individual steps. This adds significant time and cost to the fabrication of this type of photospectrometer.

Fabry-Perot filters with silver reflective layers are also known to have relatively low transmission, especially in the blue portion of the spectrum, and tend to produce a second harmonics peak in the red wavelength band, which can add noise to the output signal of the photospectrometer. Additionally, since these filters include metal layers on their top and bottom, the bottom metal layer can contaminate the integrated photodiode array, and the top metal layer generally requires additional insulating layers to protect against humidity and human handling.

Figure 3:
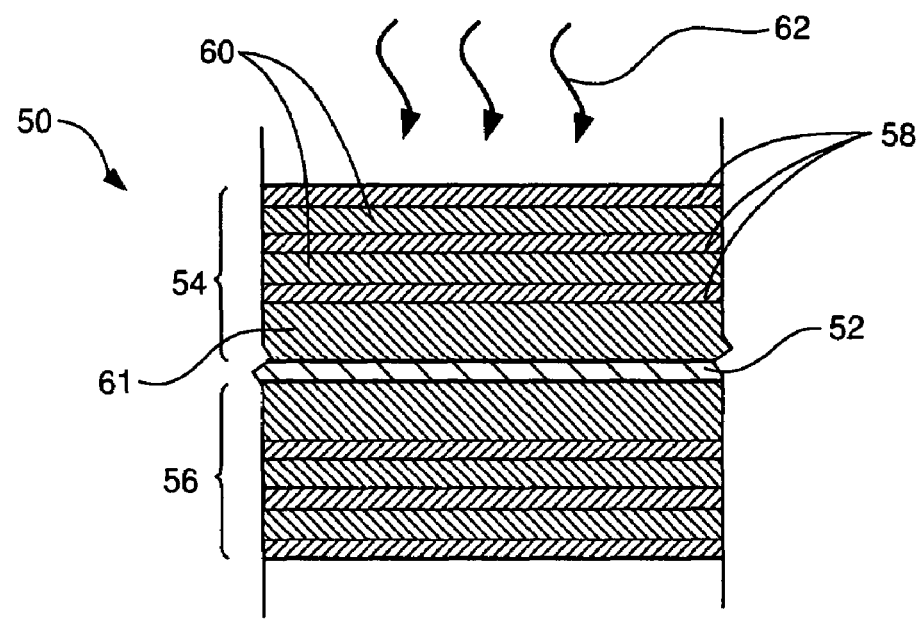
FIG. 3 is a partial cross-sectional view of one embodiment of a thin film Multi-Layer optical Coating (MLC) filter.

Advantageously, the inventors have developed a linearly variable wedge-shaped thin film multi-layer optical coating (MLC) filter that has some advantages over the standard Fabry-Perot filter. A non-wedge-shaped embodiment of such a thin film filter 50 is shown in FIG. 3. The filter comprises one and only one partially reflective metal layer 52 that is sandwiched between two transparent layers 54, 56. Each transparent layer includes alternating layers of dielectric material of different thicknesses and having different properties. For example, each transparent layer can have three layers 58 of a first dielectric material, alternating with three layers 60, 61 of a different dielectric material. The top and bottom transparent layers are identical, though inverted from each other. As with a Fabry-Perot filter, undesired wavelengths of the incident light 62 are filtered out through interference, depending upon the thickness of the different dielectric layers, and their refractive indices. Ultimately, a certain wavelength band of light will exit the bottom transparent layer 56.

In one embodiment, the inventors prepared a thin film multi-layer optical coating filter like that shown in FIG. 3 having six alternating layers of two different dielectric materials (e.g. one material having a refractive index that is higher than the refractive index of the other) in each transparent layer 54, 56. In this embodiment, the first third and fifth layers 58 were of titanium dioxide ($TiO_2$) and had a thickness of about 51.46 nm. The second and fourth layers 60 were of silicon dioxide ($SiO_2$) and had a thickness of about 86.69 nm. The sixth layer 61 of each transparent layer (the layer positioned adjacent to the partially reflective metal layer) was of silicon dioxide ($SiO_2$) and had a thickness of about 152.58 nm. The metal layer 52 was a layer of aluminum (Al) having a thickness of about 14 nm.

This non-wedge shaped filter passed a high, narrow band of light at the 500 nm wavelength range. A plot of the pass band curve is shown at 152 in FIG. 6. As can be seen, this filter provided a peak transmission efficiency of about 85% at this wavelength.

Figure 4:
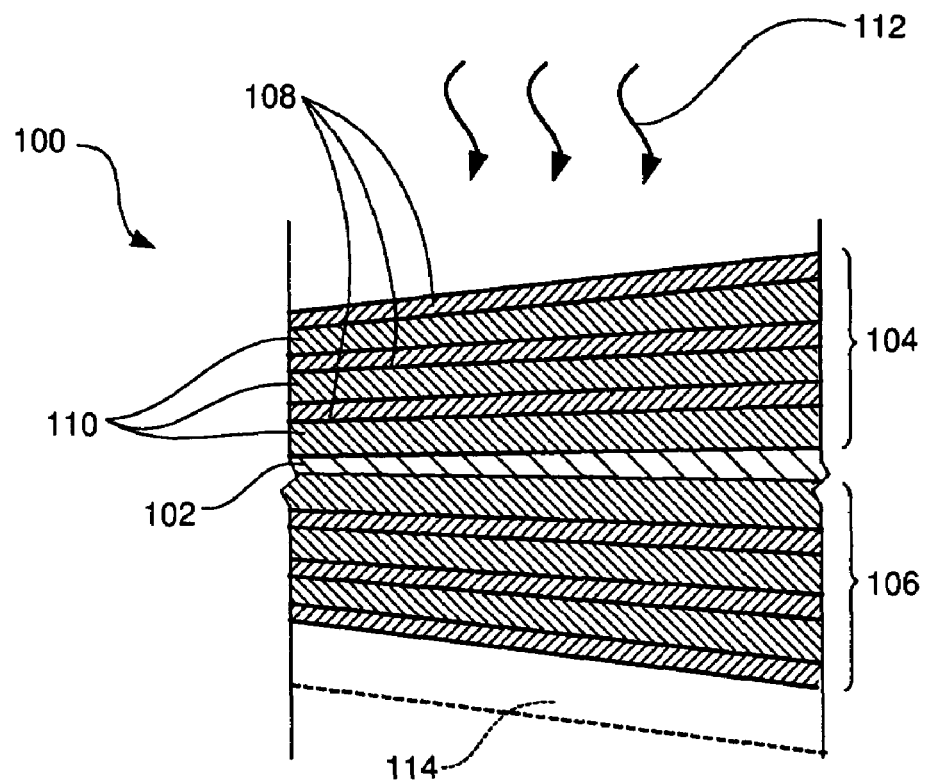
FIG. 4 is a partial cross-sectional view of one embodiment of a wedge shaped linearly variable thin film multi-layer optical coating filter having a wedge profile.

In order to provide a linearly variable filter, the inventors have produced a thin film multi-layer optical coating filter like that of FIG. 3 in a wedge profile, as shown in FIG. 4. In the wedge-shaped thin film multi-layer optical coating filter 100 the metal layer 102 and each transparent layer 104, 106 have a wedge profile that is thinner toward one end and thicker toward the other. In one embodiment, the inventors have found that a wedge profile providing about a 45% thickness increase from one end of the filter the other provides sufficient variability. In other words, the thickness of the filter at the thick end will be about 45% greater than the thickness at the thin end. This variation in thickness is only one example. Other wedge profiles can also be used. It should also be noted that the wedge profile is greatly exaggerated in FIG. 4 for illustrative purposes.

All of the layers of the filter 100 linearly increase in thickness in the same direction from one end of the filter to another, which can be referred to as a wedge direction. The wedge profile provides a linearly varying filter because the wavelength of light that is passed varies depending upon the thickness of all of the layers. Because all of the layers linearly vary in thickness, the wavelength of light that will pass through the filter will vary linearly from one edge of the filter to another. This wedge profile allows sufficient variability to selectively allow passage of light throughout the visible spectrum. It will be apparent, however, that this type of filter can be used to filter light that is outside the visible spectrum.

This linearly variable light filter 100 thus includes one and only one partially reflecting layer 102 having a wedge-shaped profile. The first transparent layer 104 is disposed atop the partially reflecting layer, and the second transparent layer 106 is disposed on the bottom of the partially reflecting layer. A transparent substrate 114 can be provided adjacent to either or both of the top and bottom of the filter. Suitable materials for the partially reflecting layer include metals such as aluminum, silver, copper, gold, nickel, tin, chromium, etc. Other reflective materials can also be used. Silver and aluminum are considered suitable materials for the partially reflective layer. Aluminum is desirable because of its low cost and ease of use in semiconductor fabrication techniques. Silver is desirable because of its relatively high reflectivity and other optical properties. In general, metals are suitable because they tend to be good reflectors in the visible and infrared ranges, though metals can present various absorption characteristics in different wavelength ranges. For example, copper shows some light absorption below 500 nm, while silver does not absorb light in the visible range to the same extent as copper. Consequently, different metals can be used for different wavelength targets. Those of skill in the art will be able to select a suitable material for the partially reflective layer.

A transparent substrate (e.g. glass, silicon, etc.) can be disposed below the second transparent layer 106 and/or above the first transparent layer 104. The use of a substrate layer can be convenient for fabrication. For example, the wedge-shaped filter can be fabricated upon a glass substrate that will provide a window or lens into a photospectrometer chip. Alternatively, the thin film multi-layer optical coating can be fabricated directly atop an array of photodiodes as part of a photospectrometer, the array serving as the substrate. Other substrates can also be used.

Each transparent layer comprises at least three layers of material of differing characteristics, each layer having a wedge-shaped profile oriented in the wedge direction. In one embodiment, the transparent layers can each comprise at least three layers of dielectric material. The number of layers in each transparent layer can vary, from as few as three layers, to any number of layers. The inventors have found that fewer layers tends to decrease the resolution of the filter, while more layers increases internal reflectivity and narrows the bandwidth. A greater number of layers also appears to enhance transmission and reduces noise, though it also increases fabrication cost. The inventors believe that more than 22 layers begins to become impractical. Suitable dielectric materials for the transparent layers include titanium dioxide ($TiO_2$), silicon dioxide ($SiO_2$), tantalum oxide (TaO), niobium oxide (NbO), aluminum oxide (AlOx), zinc oxide (ZnOx), tellurium oxide (TeOx), hafnium oxide (HfOx), etc. Other materials can also be used. Those of skill in the art will be able to select suitable materials for the transparent layers.

The inventors have found that six dielectric layers in each transparent layer is a workable configuration (thus producing a thin film multi-layer optical coating having 13 total layers—six layers on top, one metal layer, and six layers on the bottom). This configuration is shown in FIG. 4. The top transparent layer 104 includes first, third, and fifth layers 108 of a first dielectric material, and second, fourth and sixth layers 110 of a second dielectric material. The top and bottom transparent layers 104, 106 are identical, but inverted relative to each other. That is, the material types and thicknesses occur in the reverse order in the bottom layer, compared to the top layer, when each is considered from the top down. Incident light 112 is selectively passed through the filter depending upon the thickness of all of the layers at a given point along the filter.

As discussed above with respect to the non-wedge-shaped embodiment of FIG. 3, the first and second transparent layers can each comprise alternating layers of two different dielectric materials of two different thicknesses, and a third thickness of one of the two dielectric materials in a layer adjacent to the partially reflecting metal layer. In one embodiment this can comprise six alternating layers of two different dielectric materials in each transparent layer. Alternatively, the thicknesses of the respective dielectric layers can vary randomly within each transparent layer. That is, rather than two or three discrete thicknesses for the layers of alternating material, each layer can have a thickness that differs from each of the others. It will be apparent that, using a six layer configuration like that shown in FIG. 3, but having a wedge shaped profile as shown in FIG. 4 can provide the actual combination of layer thicknesses discussed above (with respect to FIG. 3) at one discrete location along the wedge profile. These thicknesses will decrease proportionally in one direction from that location, and increase proportionally in an opposite direction from the location. In one embodiment, the linearly variable filter having a wedge profile can have a partially reflecting metal layer of aluminum with a thickness that ranges from about 10 nm to about 30 nm, and first and second transparent layers of alternating layers of titanium dioxide ($TiO_2$), silicon dioxide ($SiO_2$), each stack having a total thickness that ranges from about 30 nm to about 150 nm from one end of the wedge shaped filter to the other.

Figure 5:
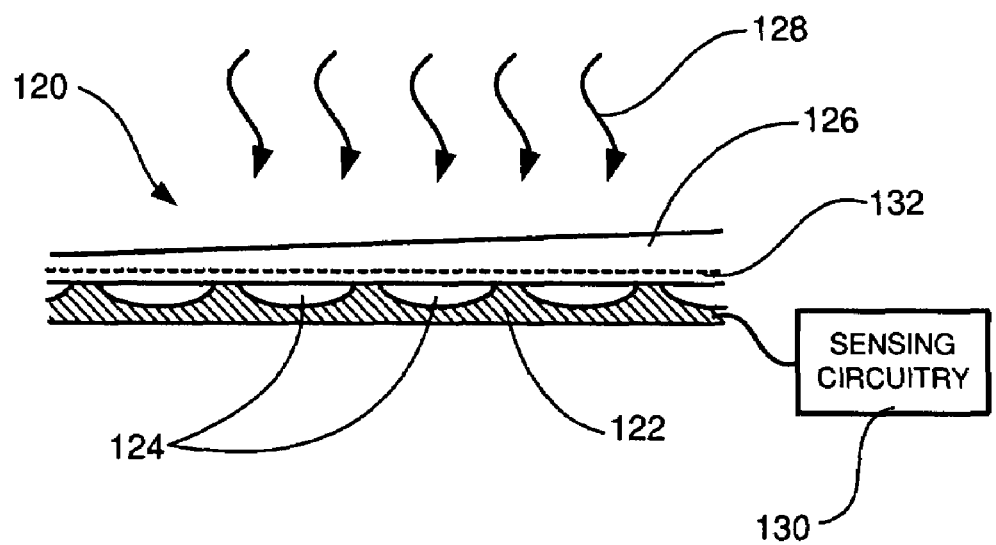
FIG. 5 is a partial cross-sectional view of one embodiment of a solid state photospectrometer comprising an array of photodiodes having a wedge shaped linearly variable thin film multi-layer optical coating filter.

Advantageously, this wedge-shaped design can be produced using a single deposition process, and provides good film quality and accurate thickness control, while also reducing deposition time and cost compared to a standard Fabry-Perot filter. As shown in FIG. 5, when this type of filter 126 is coupled with an array of photodiodes 124, it can provide a photospectrometer 120 with multiple wavelength sensitivity using one continuous filter, rather than having separate discrete filters for each photodiode. The photospectrometer generally includes a substrate 122 having a plurality of photodiodes 124 disposed thereon. Each photodiode is electrically coupled to sensing circuitry 130, the circuitry configured to receive a signal representative of light intensity sensed by the photodiode. Incident light 128 is filtered by the variable thin film filter 126, so that each photodiode receives a different wavelength band of light. As suggested above, in one embodiment, the wedge shaped filter can be disposed upon a transparent substrate 132, this transparent substrate overlying the array of photodiodes.

The linearly variable light filter is disposed over the array of photodiodes, and, as described above, includes one and only one partially reflecting metal layer having a wedge profile, with a first transparent layer as described above disposed on top of the metal layer, and a second transparent layer disposed on the bottom of the metal layer. Each transparent layer includes at least two dielectric layers of differing materials, and each dielectric layer has a wedge-shaped profile oriented in the wedge direction. This configuration allows a different wavelength band of light to be provided to each photodiode, depending upon the total thickness of the linearly variable light filter at the position of the particular photodiode.

Figure 6:
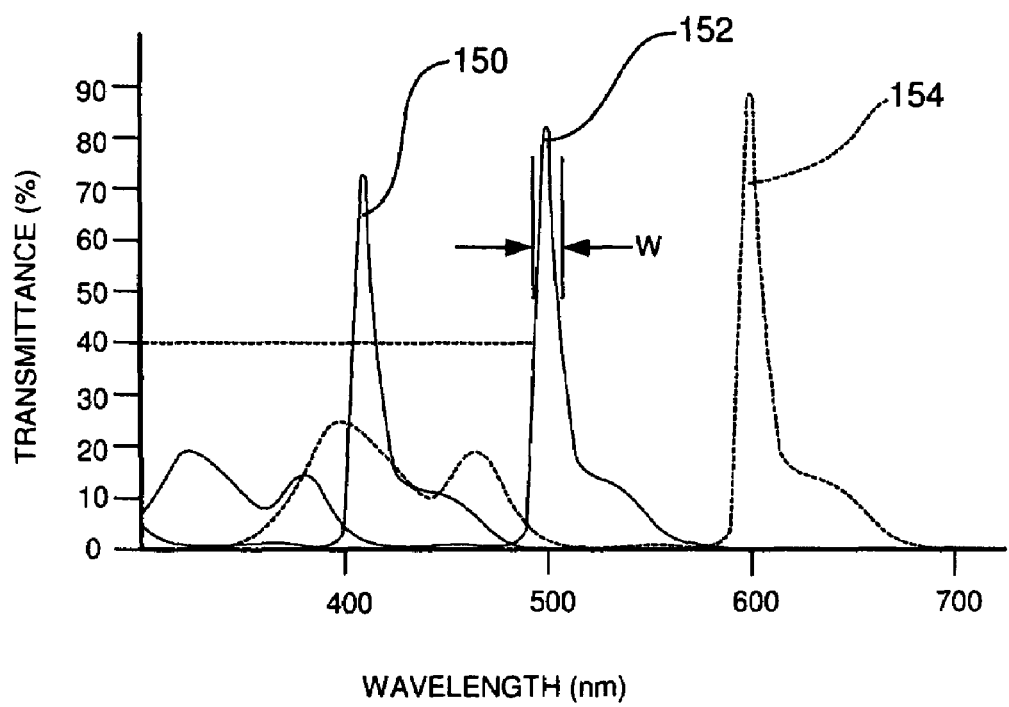
FIG. 6 is a graph of light transmission versus wavelength for three discrete regions of an embodiment of a linearly variable filter configured in accordance with the present disclosure.

The inventors have found that the linearly variable thin film multi-layer optical coating filter provides relatively high transmission of light. For example, as shown in FIG. 6, a linearly variable filter as described herein can provide wavelength peaks at various desired wavelengths. It can be seen that the transmission of light at each wavelength peak is quite high. The inventors have found that this linearly variable filter will pass from about 75% to about 90% of light over the entire visible spectrum, the lower transmission being toward the blue end of the scale. For example, one embodiment of a photospectrometer provided with a linearly variable MLC as described herein can provide a peak 150 at a wavelength of around 400 nm, with another peak 152 at about 500 nm. Additional transmission peaks can also be provided, such as the peak 154 at around 600 nm. Each of these peaks provides more than 70% transmission efficiency. In contrast, a typical Fabry-Perot filter tends to provide only about 20% to 50% transmission in the visible spectrum.

Another feature of this filter configuration is that the bandwidth at each desired wavelength (i.e. the width W of each peak on the transmittance graph of FIG. 6) can be selected by varying the characteristics (i.e. the materials and layer thicknesses) of the thin film multi-layer optical coating. The bandwidth W is typically measured as the width of the transmission peak at a level that is half of the peak value. This is referred to as the full-width half max (FWHM) value. In FIG. 6, for the 500 nm peak 152m having a maximum transmission of about 80%, the FWHM value is the width of the peak measured at about the 40% level, as shown. Each different film thickness design (i.e. combination of layer thicknesses) will produce a different FWHM bandwidth. This approach can allow one to adjust the design to narrow the bandwidth without a trade off in transmission performance. It is to be noted that changes in the overall wedge profile do not significantly affect the targeted FWHM. The inventors have found that in the wedge shaped thin film multi-layer optical coating disclosed herein the bandwidth can be adjusted from about 5 nm to about 30 nm FWHM without a loss of transmission efficiency through careful selection of the thin film materials and thicknesses. The Fabry-Perot approach, on the other hand, only allows adjustment of the bandwidth from about 20 nm to about 40 nm, and also involves a tradeoff in transmission efficiency (i.e. less transmission as the bandwidth narrows).

The linearly variable thin film multi-layer optical coating filter with a wedge-shaped profile allows infinite transmission bands to be chosen without requiring multiple etching and deposition steps in the filter fabrication. The thin film multi-layer optical coating filter can be produced using aluminum for the metal layer, which is less expensive and more fabrication-friendly than silver. This configuration also promotes good film quality and accurate thickness control, and reduces the quantity of deposition materials needed, and the fabrication time and cost compared to other methods.

This configuration also provides high transmission throughout the visible spectrum, relatively narrow bandwidth peaks (i.e. providing high finesse) and a greater range of adjustability in bandwidth. Another desirable aspect of the linearly variable thin film multi-layer optical coating filter disclosed herein is that it does not produce a second order harmonics peak, as does a standard Fabry-Perot filter. Additionally, since the wedge-shaped filter includes transparent dielectric layers on top and on the bottom, the filter naturally has excellent electrical isolation from photodiode circuitry underneath, and the upper dielectric layer provides protection from oxidation, humidity, and potential adhesion with other structures.

It is to be understood that the above-referenced arrangements are illustrative of the application of the principles of the present invention. It will be apparent to those of ordinary skill in the art that numerous modifications can be made without departing from the principles and concepts of the invention as set forth in the claims.

What is claimed is:

1. A light filter, comprising:
   exactly one partially reflective layer having a top and a bottom and a wedge-shaped profile defining a wedge direction;
   a first transparent layer, disposed atop the partially reflective layer, comprising at least three dielectric layers of two different materials, each dielectric layer having a wedge-shaped profile oriented in the wedge direction;
   a second transparent layer, disposed on the bottom of the partially reflective layer, comprising at least three dielectric layers of two different materials, each dielectric layer having a wedge-shaped profile oriented in the wedge direction.

2. A light filter in accordance with claim 1, wherein each of the first and second transparent layers comprise at least three layers of dielectric material having different and substantially randomly varying thicknesses.

3. A light filter in accordance with claim 1, wherein the first and second transparent layers each comprise alternating layers of two different dielectric materials of two different thicknesses, and a third thickness of one of the two dielectric materials in a layer adjacent to the partially reflective layer.

4. A light filter in accordance with claim 3, wherein the first and second transparent layers each comprise six alternating layers of the two different dielectric materials.

5. A light filter in accordance with claim 4, further comprising a discrete position along the filter wherein the six alternating layers of the two different dielectric materials comprise first third and fifth layers of titanium dioxide (TiO$_2$) having a thickness of about 51.46 nm, second and fourth layers of silicon dioxide (SiO$_2$) having a thickness of about 86.69 nm, and a sixth layer of silicon dioxide (SiO$_2$) having a thickness of about 152.58 nm, the sixth layer being positioned adjacent the partially reflective layer, and the partially reflective layer comprises a layer of aluminum (Al) having a thickness of about 14 nm.

6. A light filter in accordance with claim 1, wherein the two different dielectric materials are selected from the group consisting of titanium dioxide (TiO$_2$), silicon dioxide (SiO$_2$), tantalum oxide (TaO), niobium oxide (NbO), aluminum oxide (AlOx), zinc oxide (ZnOx), tellurium oxide (TeOx) and hafnium oxide (HfOx).

7. A light filter in accordance with claim 1, wherein the partially reflective layer is of a material selected from the group consisting of aluminum, silver, copper, gold, nickel, tin and chromium.

8. A light filter in accordance with claim 1, wherein the wedge profile comprises about a 45% thickness increase from a first end of the linearly variable filter to a second end thereof.

9. A light filter in accordance with claim 1, wherein the partially reflective layer has a thickness that ranges from about 10 nm to about 30 nm, and the first and second transparent layers have a total thickness that ranges from about 30 nm to about 150 nm.

10. A light filter in accordance with claim 1, further comprising a transparent substrate, disposed against one of the first and second transparent layers.

11. A light filter, comprising:
    exactly one partially reflective layer having a top and a bottom and a wedge-shaped profile defining a wedge direction;
    a first transparent layer, disposed on top of the partially reflective layer, comprising at least two dielectric layers of differing materials, each dielectric layer having a wedge-shaped profile oriented in the wedge direction; and
    a second transparent layer, disposed on the bottom of the partially reflective layer, comprising at least two dielectric layers of differing materials, each dielectric layer having a wedge-shaped profile oriented in the wedge direction.

12. A light filter in accordance with claim 11, wherein the first and second transparent layers each comprise alternating layers of two different dielectric materials of two different thicknesses, and a third thickness of one of the two dielectric materials in a layer adjacent to the partially reflective layer.

13. A light filter in accordance with claim 12, wherein the two different dielectric materials are selected from the group consisting of titanium dioxide (TiO$_2$), silicon dioxide (SiO$_2$), tantalum oxide (TaO), niobium oxide (NbO), aluminum oxide (AlOx), zinc oxide (ZnOx), tellurium oxide (TeOx) and hafnium oxide (HfOx), and the partially reflective layer is of a material selected from the group consisting of aluminum, silver, copper, gold, nickel, tin and chromium.

14. A light filter in accordance with claim 11, wherein the wedge profile comprises about a 45% thickness increase from a first end of the linearly variable filter to a second end thereof, the partially reflective layer having a thickness that ranges from about 10 nm to about 30 nm, and the first and second transparent layers each having a total thickness that ranges from about 30 nm to about 150 nm.

15. A light filter in accordance with claim 11, further comprising a transparent substrate, disposed against one of the first and second transparent layers.

16. A photospectrometer, comprising:
    a substrate;
    a plurality of photodiodes disposed upon the substrate, each photodiode being electrically coupled to sensing circuitry for receiving a signal representative of light intensity sensed by the respective photodiode; and a light filter disposed over the photodiodes, comprising
exactly one partially reflective layer having a top and a bottom and a wedge-shaped profile defining a wedge direction;

a first transparent layer, disposed on top of the partially reflective layer, comprising at least three dielectric layers of two differing materials, each dielectric layer having a wedge-shaped profile oriented in the wedge direction;

a second transparent layer, disposed on the bottom of the partially reflective layer, comprising at least three dielectric layers of two differing materials, each dielectric layer having a wedge-shaped profile oriented in the wedge direction.

17. A photospectrometer in accordance with claim 16, wherein the first and second transparent layers each comprise alternating layers of two different dielectric materials of two different thicknesses, and a third thickness of one of the two dielectric materials in a layer adjacent to the partially reflective layer.

18. A photospectrometer in accordance with claim 17, wherein the two different dielectric materials are selected from the group consisting of titanium dioxide ($TiO_2$), silicon dioxide ($SiO_2$), tantalum oxide (TaO), niobium oxide (NbO), aluminum oxide (AlOx), zinc oxide (ZnOx), tellurium oxide (TeOx) and hafnium oxide (HfOx), and the partially reflective layer is of a material selected from the group consisting of aluminum, silver, copper and gold.

19. A photospectrometer in accordance with claim 16, wherein the wedge profile comprises about a 45% thickness increase from a first end of the light filter to a second end thereof, the partially reflective layer having a thickness that ranges from about 10 nm to about 30 nm, and the first and second transparent layers each having a total thickness that ranges from about 30 nm to about 150 nm.

20. A photospectrometer in accordance with claim 16, further comprising a transparent substrate, disposed below the second transparent layer and above the array of photodiodes.

* * * * *

UNITED STATES PATENT AND TRADEMARK OFFICE
CERTIFICATE OF CORRECTION

PATENT NO. : 7,576,860 B2
APPLICATION NO. : 11/801830
DATED : August 18, 2009
INVENTOR(S) : Kuohua Angus Wu et al.

It is certified that error appears in the above-identified patent and that said Letters Patent is hereby corrected as shown below:

In column 9, line 3, in Claim 16, after "comprising" insert -- : --.

Signed and Sealed this

Twenty-ninth Day of June, 2010

David J. Kappos
*Director of the United States Patent and Trademark Office*